US009782254B2

(12) United States Patent
Perera (10) Patent No.: US 9,782,254 B2
(45) Date of Patent: Oct. 10, 2017

(54) DEVICE FOR SINGLE HANDLED INJECTION OF AN INTRAOCULAR LENS (71) Applicant: SINGAPORE HEALTH SERVICES PTE LTD, Bowyer Block C (SG)

(72) Inventor: Shamira Perera, Bowyer Block (SG)

(73) Assignee: SINGAPORE HEALTH SERVICES PTE LTD, Singapore (SG)

(*) Notice: Subject to any disclaimer, the term of this patent is extended or adjusted under 35 U.S.C. 154(b) by 221 days.

(21) Appl. No.: 14/768,509

(22) PCT Filed: Feb. 21, 2014

(86) PCT No.: PCT/SG2014/000077
§ 371 (c)(1),
(2) Date: Aug. 18, 2015

(87) PCT Pub. No.: WO2014/129977
PCT Pub. Date: Aug. 28, 2014

(65) Prior Publication Data
US 2016/0000556 A1    Jan. 7, 2016

(30) Foreign Application Priority Data
Feb. 21, 2013   (SG) ................................ 201301289-3

(51) Int. Cl.
*A61F 2/16*   (2006.01)
(52) U.S. Cl.
CPC ..................................... *A61F 2/167* (2013.01)
(58) Field of Classification Search
CPC .......... A61F 2/16; A61F 2/167; A61F 2/1662; A61F 2/1675; A61F 2/1678; A61F 2/1667
See application file for complete search history.

(56) References Cited

U.S. PATENT DOCUMENTS 4,834,094 A * 5/1989 Patton ................... A61F 2/1662
606/107
5,520,658 A    5/1996 Holm
(Continued)

FOREIGN PATENT DOCUMENTS

WO    9637152    11/1996
WO    9726841    7/1997
(Continued)

OTHER PUBLICATIONS

International Publication and International Search Report for PCT/SG2014/000077.

*Primary Examiner* — Victor Nguyen
(74) *Attorney, Agent, or Firm* — Soroker Agmon Nordman (57) ABSTRACT

A device 100 for delivering intraocular lens into an incision on an eye of a patient comprises a tubular member 130 defined by a hollow elongate passageway 131, a front 132 and a back through opening 133 of the passageway 131; a secured nozzle 150 having an expanded base 152, which is mounted to the front through opening 132 of the tubular member 130, tapering towards a pointed end 153 fashioned to be inserted into the incision, the secured nozzle 150 enclosing a lumen 154 substantially tapered from the base 152 to the pointed end 153 and aligned with the passageway 131 that the lens is disposed within the lumen 154 to be readily delivered; an elongate probe 110, at least partially housed within the passageway 131, having a bifurcated tip 115 which is configured to telescopically slide out from the pointed end 153 of the secured nozzle 150 pushing the disposed lens into the eye; and a plunger assembly 120 having a shaft 126 inserted into and moveable within the passageway 131 to anteriorly engage with the probe 110 to move the probe 110 in relative to the tubular member 130, wherein the bifurcated tip 115 forks into a first 111 and (Continued)

second prongs 112, which are irregular in size, forming a substantially U-shaped or V-shaped construct thereof for manipulating a configuration and/or and orientation of the delivered lens in the eye.

13 Claims, 9 Drawing Sheets

(56) References Cited

U.S. PATENT DOCUMENTS

| | | |
|---|---|---|
| 5,766,181 A | 6/1998 | Chambers |
| 7,879,090 B2 * | 2/2011 | Pynson ................ A61F 2/1678 606/107 |
| 2005/0090781 A1 | 4/2005 | Baba |
| 2012/0191102 A1 | 7/2012 | Matsumoto |

FOREIGN PATENT DOCUMENTS

| | | |
|---|---|---|
| WO | 9959668 | 11/1999 |
| WO | WO2012/027517 A2 | 3/2012 |

* cited by examiner

DEVICE FOR SINGLE HANDLED INJECTION OF AN INTRAOCULAR LENS

TECHNICAL FIELD

This application claims priority to the following patent applications; (1) Singapore patent application no. 201301289-3 filed Feb. 21, 2013, and (2) PCT application no. PCT/SG2014/000077 filed on Feb. 21, 2014 which is incorporated by reference herein.

The present invention relates to an ophthalmic surgical device for delivering a deformable intraocular lens (TOL) of various configurations. More specifically, the disclosed invention features a probe capable of manipulating the orientation of an IOL in response to user interaction with the probe upon loading the IOL into an eye of a patient. The disclosed invention is also fashioned to be operated single-handedly by the user.

BACKGROUND OF THE INVENTION

In order to generate visual perception, the light reflected from an object to be perceived must be transmitted through the eye's cornea and focused onto the retina by the crystalline lens of the eye. The aging process or disease states tend to result in diminished functionality or transparency of the crystalline lens, which further leads to deteriorated vision. The degraded visual perception owing to lens damage can be restored through replacing the faulty crystalline lens with a human made artificial lens, or a so-called intraocular lens (IOL). The faulty crystalline generally has to be removed via a surgical procedure, which involves creating a small incision in the anterior capsule where the crystalline lens is located; liquefying the crystalline lens; extracting the liquefied lens; and inserting the IOL into the capsule for replacement using an IOL injecting device.

To squeeze through the small incision made in the cornea, the injection requires the IOL to be temporarily folded or deformed, and the IOL only resumes its original configuration once deposited into the eye successfully. It is possible to create an incision of larger size to facilitate the injection process, but an incision of greater size commonly results in a prolonged healing period and induced astigmatism. Consequently, effort has been put into developing IOLs and the injection devices intended for IOL delivery through incisions sized 3 mm and below. In the past, most of the problems associated with lens insertion have been addressed primarily by improvements in lens design, and to a lesser extent better machined lens cartridges and more sophisticated lens injectors. Particularly, the IOLs with greater resistance against scratching or tearing during the injection process are fabricated from a wide variety of materials like hydrogel, silicon hydrogels, hard polymethyl methacrylate, acrylic resin, and 2-hydroxyethyl methacrylate. Further, improvement is made in IOL configuration. For example, IOLs with plate-shaped haptics have been produced. However, some problems still exist in both the loading step and the actual IOL insertion.

In general, IOL injection devices are designed to be operated single- or two-handed. Most present day commercially available injectors require a two handed approach using a pepper mill action. For instance, Zaleski in U.S. Pat. No. 5,643,276 discloses an injection device furnished with a rotational assembly that can be dialed distally to controllably rotate a rod delivering the lens through an insertion tube inserted into the incision. Another U.S. Pat. No. 7,892,282 provides another rotatably operable lens delivering device by which constant rotation of a drive mechanism on the device causes discrete forward or backward movement of the rod engaging the lens. On the other hand, various single handed devices have been attempted, most resembles a hypodermic syringe. These devices have a tubular body incorporated with a telescopically moveable plunger at one end, and another extreme end with a tapered tip to be inserted into the eye. The plunger pushes the lens, formerly stored in the body of the device or a cartridge attached thereto, into the eye through the tapered tip. An explosive delivery, a tendency of the lens to float upwards, the undesired pushing away of the eye, a non-ergonomic fit in the hand, and a requirement for a large manual expulsion force mean that these IOL injection devices have not been adopted widely. Corresponding injection tools have been devised in respect to some of the above mentioned shortcomings Kobayashi et al. describes a single-handedly operable injection device provided with a posture control member to avoid damaging the IOLs caused by expulsion force induced-deflection at the plunger end engaged to the lens. Further, U.S. Pat. Nos. 6,162,229 and 8,535,332, respectively, offer injection tools carrying a uniquely made plunger tip to expel the IOL from the injector body into the eye in a non-destructive and controlled manner. However, handling these enhanced single-handed IOL injection devices in practical use can be difficult despite the solutions offered to protect the IOL during delivery. Particularly, the dimensions of the prolonged lens delivering tubular body and the bifurcated handles of such injection tools substantially mimic an injection syringe rather than being ergonomically designed to serve IOL delivery. There exist significant differences with regards to administration site and the subject matter to be delivered between an injection syringe and an IOL delivering device. For instance, an IOL delivery procedure can require substantial amount of time to be spent in manipulating the configuration and orientation of the deposited lens, in comparison with medicine injection. In view of this, an IOL injection device that is single-handedly operable and which remedies the aforesaid shortcomings is desired.

SUMMARY

One object of the present invention relates generally to providing an intraocular lens (IOL) injection or delivery device that can deliver and place an IOL more easily, with more controlled manipulation during cataract surgery. The IOL injection device can deliver any commercially available injectable intraocular lens through a variety of incision sizes utilizing a single-handed approach.

Another object of the present invention is to provide a device having an advancement mechanism attached to a gently depressible trigger, which can be used to slowly push the IOL through the incision, preferably with minimal force exerted. The disclosed device utilizes an advancement mechanism attached to a gently depressible trigger, which can be used to slowly insert and push the lens through the incision with minimal force exerted. The clear advantage of any one handed system is that it leaves the surgeon's other hand free to fixate the eye at all times, minimize patient movement, and if necessary, direct the IOL into the correct place, position, or orientation. This could be either an ideal or near-ideal "in the bag" placement of the lens, or placement at a particular meridian to address zonular laxity, or even sulcus placement when there has been a complication such as posterior capsular rupture. Alternatively, for in the bag placement of a toric lens, the surgeon's free hand can be used to guide the lens into a near-correct orientation, after which fine-tuning of the lens position can occur without the inelegant procedure of rotating an unfolded lens in the bag. This can have the advantages of causing less stress of the zonules and saving time by not having to rotate the whole lens in the bag by up to 90 degrees. This procedure allows the lens to be tightly packaged as a pellet which can be inserted in a correct orientation and then allowed to slowly unfold with a tap of the surgeon's non-dominant hand. This converts a previously unwanted feature of the sticky nature of the haptics (which sometimes stick to each other and/or the optic of the lens itself) into a positive advantage that is currently available.

Another object of the present invention is to provide a Y-shaped plunger, preferably with a V-shaped or C-shaped bifurcated tip, enabling a smooth and non-explosive delivery of the IOL into the eye. Once the lens is inside the eye, the tip can also be fully extended and used to fine tune the orientation of the lens, in particularly for toric lenses, together with another instrument if needed. Hence, the plunger can be considered as a manipulator inside the eye. The Y shaped plunger is also specially designed to be able to manipulate the lens in the eye. This ability to manipulate the lens in the eye within a closed chamber is unique and offers the highest degree of control of the patient's eye in 3 dimensions during insertion and placement of the lens. This is particularly useful if the patient is moving their eye. The pellet form of insertion would enable easier insertion of toric lenses especially, and pave the way for a new type of preloaded lenses. These would offer a completely preloaded system, which would circumvent complex loading systems, e.g., the HOYA 250 lens, whilst still offering the advantages of a loaded lens.

Still, an object of the present invention is to provide an IOL delivery or injection device incorporated with ergonomic features to facilitate single-handed operation. Particularly, the disclosed device possesses multiple support or anchorage points to stably rest the device on the face area of the patient throughout the operation. More preferably, the disclosed device is fashioned to be used with at least a portion of the bottom ridge of the hand of the surgeon or user resting on the face area of the patient to improve stability of the hand operating the device. The single-handed operation allows for lens insertion through smaller incisions without the need for especially thin or deformable lenses, by using wound-assisted delivery of the lens. The injector mechanism itself can be further scaled for pre-loaded systems whereby a plastic preloaded 'package' with a tightly preloaded IOL which requires no manipulation (unlike present day versions) can be attached to the trigger mechanism.

A further object of the disclosed invention provides an IOL injection tool designed for operation in a pistol-like or gun-like fashion to optimize the fit in between the disclosed tool and the user. Specifically, this lens injection tool or gun has the potential to revolutionize lens insertion as it delivers the lens with a steadied grip, in a predictable and controlled manner, and frees up the surgeon's other hand. Uniquely, the surgeon's hand that holds the IOL injection tool can be stabilized on the patient's cheek or head in a way that cannot be achieved with either the two handed pepper mill type injectors or single handed hypodermic type injectors.

One of the objects of the present invention is to provide an IOL injector equipped with additional structural features to function as a lens manipulator. The injector disclosed herein possesses a probe carrying a V-shaped or U-shaped bifurcated tip that can be inserted into the eye to manipulate an injected lens. Collectively, the bifurcated tip and the plunger assembly form a substantially Y-shaped plunger.

The Y-shaped plunger enables a smooth and non-explosive delivery of the lens, and once the lens is inside the eye, the Y-shaped plunger can also be used fully extended to fine tune the orientation of the lens (in particular for toric lenses) together with another instrument if needed. This is in contrast to other plungers that use a bulky soft tip that cannot be used inside the anterior chamber, or plungers which have a less functional spatulated end. With the pepper mill type injectors, the plunger is by definition rotated to push the lens into the eye. This means that the plunger may not be in the correct orientation for use once inside the eye. However, with rack and pinion single handed insertion, the plunger is always in the correct orientation and needs only a rotation of the surgeon's wrist to align it, instead of another turn of the screw for the pepper mill type injector. This invention provides a novel plunger usable for manipulation of the lens inside the eye. Currently, another instrument has to be inserted after lens insertion to rotate the lens into the correct position. The advantage of having this instrument already available on the end of the plunger is that it saves unnecessary movement into and out of the eye, and it offers a stable enclosed chamber for 2 handed manipulation.

When these advantages are coupled with the fact that the disclosed IOL injection device can fit various different cartridge systems, there can be efficiency through a move towards a universal injector system. The single handed approach to injection also confers other advantages. If, for example, the lens has been incorrectly placed in the cartridge, or has twisted during its insertion into the eye, it is far easier to manipulate the IOL injection device with one hand during a remedial technique, rather than in the case of the pepper mill type inserter, which requires more manual dexterity as the "mill" and rotatory plunger have to be manipulated separately whilst being coordinated. With the injector disclosed herein, the surgeon's other hand can be used to fine tune the placement of the lens once inside the eye, and the plunger can rotate the lens.

It is important to be noted that the IOL injection device disclosed herein further leverages on the fact that lens design across a variety of platforms is converging towards a uniform one piece, planar (non vaulted) structure. Although there are still a large number of lens types in routine use, most can be injected by way of the universal cartridge and injector system disclosed herein. A one piece design which is essentially inserted as a pellet into the bag which slowly unfolds upon being touched with a Sinskey hook/Macpherson's forceps is quite different from the 3 piece lenses with PMMA haptics which could move around and cause complications. This would aid in the placement of toric lenses in that the pellet form (haptics not unfolded form) of the lens can be rotated in the bag in either a clockwise or anticlockwise direction quite easily, unlike the clockwise only direction that can be used for unfolded haptic configuration of the lens. If a lens is rotated too far beyond the correct orientation, it must be completely rotated through nearly 180 degrees to allow such over-rotation to be corrected. This could lead to complications such as posterior capsular rupture or zonular dialysis. The pellet form of the lens can be more easily manipulated, especially for toric lenses. This convergence in lens design for a universal type injector, ideally with a single handed approach, leads to an easier learning curve for less experienced surgeons and allows the easier uptake of novel lenses. There are examples of good lenses for which uptake has unfortunately been retarded, simply because of problems with a proprietary injector (e.g., B and L M160 and Akreos lens and the hypodermic type injector for the AR40 by AMO). This therefore underlines the importance of a universal type of single handed injector system disclosed herein, which is easy to use.

At least one of the preceding objects is met, in whole or in part, by an IOL injection device in accordance with an embodiment of the present invention, in which one of the embodiments involves a device for delivering intraocular lens into an incision on an eye of a patient comprising a tubular member defined by a hollow elongate passageway, a front and a back through opening of the passageway; a nozzle having an expanded base, which is mounted onto the front opening of the tubular member, tapering towards a pointed end fashioned to be inserted into the incision, the nozzle enclosing a lumen substantially tapered from the base to the pointed end and aligned with the passageway that the lens is disposed within the lumen to be readily delivered; an elongate probe, at least partially housed within the passageway, having a bifurcated tip which is configured to telescopically slide out from the pointed end of the nozzle pushing the disposed lens into the eye; and a plunger assembly having a shaft inserted into and moveable within the passageway to anteriorly engage with the probe to move the probe in relative to the tubular member, wherein the bifurcated tip forks into a first and second prongs, which are irregular in size, forming a substantially U-shaped or V-shaped construct thereof for manipulating a configuration and/or an orientation of the delivered lens in the eye. Preferably, the first and second prongs are sized in a ratio of 18-15:12-6, or more preferably in a ratio of 16:9 or 4:3.

In one embodiment of the disclosed device, the plunger assembly has an enlarged end disposed around the back opening to control movement of the plunger assembly in relative to the tubular member.

In another embodiment, the plunger assembly has a posterior end connected substantially median of a prolonged piece, exposed adjacent to the back opening, expanding in perpendicular to or at a tilted angle towards the plunger assembly and fashioned to be pushed forth or back to control movement of the plunger assembly in relative to the tubular member that the plunger assembly and the prolonged piece collectively form a T-shaped structure. Preferably, the prolonged piece has the back surface of one extreme fabricated with a depression to receive pushing force of the thumb of a user. To render the disclosed device with improved stability during its operation, the prolonged piece of the disclosed device has both ends fabricated with increased surface area, or bulges, to anchor and contact onto the face of the patient.

In one preferred embodiment, the shaft is fitted into the passageway in a single orientation by having corresponding geometrical profiles fabricated lengthwise on the inner surface of the tubular member defining the passageway and the plunger assembly.

In further preferred embodiment, the disclosed device has a handgrip extending from the external surface of the tubular member with an angle of between 50 to 80 degree formed in relative to the portion of the tubular member directing towards the front through opening that the handgrip is configured to receive middle and ring fingers of the user to space the received fingers from the pointed end of the nozzle at a distance of 4.5 to 8 cm.

Further embodiment of the disclosed device of delivering intraocular lens to an operation site of a patient comprising a tubular member defined by a hollow elongate passageway, a front and a back through opening of the passageway; a nozzle having an expanded base, which is mounted onto the front opening of the tubular member, tapering towards a pointed end fashioned to be inserted into the incision, the nozzle enclosing a lumen substantially tapered from the base to the pointed end and aligned with the passageway that the lens is disposed within the lumen to be readily delivered; an elongate probe, at least partially housed within the passageway, having a bifurcated tip which is configured to telescopically slide out from the pointed end of the nozzle pushing the disposed lens into the eye; and a driving mechanism, equipped with an actuator, mechanically engaged to the probe to move the bifurcated tip into the incision of the eye to concurrently deliver the disposed lens, wherein the bifurcated tip forks into a first and second prongs, which are irregular in size, forming a substantially U-shaped or V-shaped construct thereof for manipulating a configuration and/or an orientation of the delivered lens in the eye.

Preferably, in one embodiment, the driving mechanism comprises a rack slider stored within the passageway to anteriorly engage with the probe, and a pinion having one part functionally coupled to the rack and the other part connected to the actuator that the pinion translates motion of the actuator to move the rack forth and back in the passageway to respectively forward and retract the probe in relative to the tubular member.

In another embodiment, the driving mechanism, in fact, pivotally fixes the actuator onto the device to have one end of the actuator secured with the posterior end of the probe and another end of the actuator readily subjected to an external force to lever the forth and back movement of the probe in relative to the tubular member.

DETAILED DESCRIPTION

One having ordinary skill in the art will readily appreciate that the present invention is well adapted to carry out the objects and obtain the ends and advantages mentioned, as well as those inherent therein. The embodiment describes herein is not intended as limitations on the scope of the invention.

Figure 1:
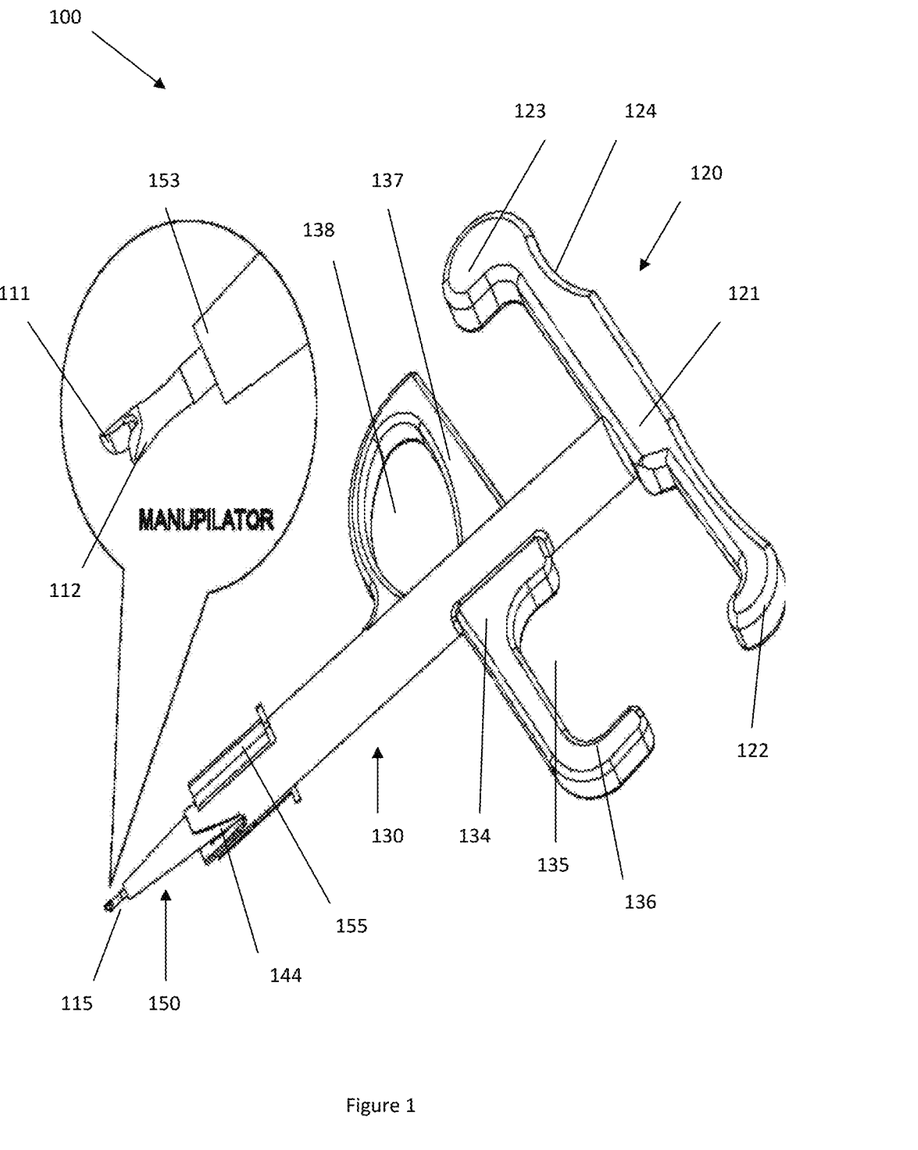
FIG. 1 illustrates one embodiment of an intraocular lens (IOL) injection or delivery device equipped with a thumb push mechanism in order to advance or retract a probe.
Figure 2:
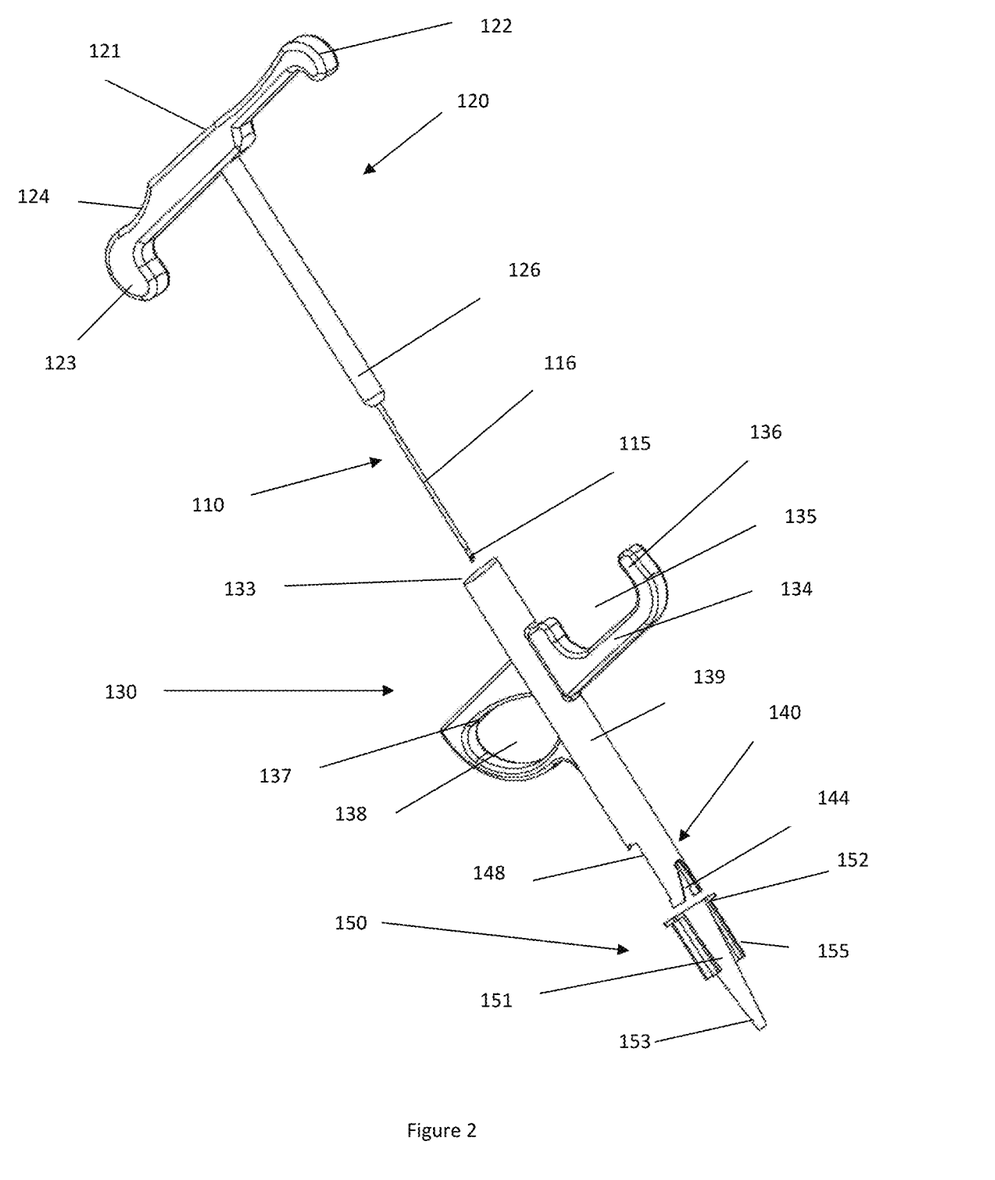
FIG. 2 illustrates an exploded view of the embodiment the disclosed device shown in FIG. 1.

As illustrated in FIGS. 1 and 2, one embodiment of the present invention is a device 100 of delivering intraocular lens into an incision on an eye of a patient comprising a tubular member 130 defined by a hollow elongate passageway 131, a front 132 and a back through opening 133 of the passageway 131; a secured nozzle 150 having an expanded base 152, which is mounted to the front through opening 132 of the tubular member 130, tapering towards a pointed end 153 fashioned to be inserted into the incision, the secured nozzle 150 enclosing a lumen 154 substantially tapered from the base 152 to the pointed end 153 and aligned with the passageway 131 that the lens is disposed within the lumen 154 to be readily delivered; an elongate probe 110, at least partially housed within the passageway 131, having a bifurcated tip 115 which is configured to telescopically slide out from the pointed end 153 of the secured nozzle 150 pushing the disposed lens into the eye; and a plunger assembly 120 having a shaft 126 inserted into and moveable within the hollow elongate passageway 131 to anteriorly engage with the probe 110 to move the probe 110 in relative to the tubular member 130, wherein the bifurcated tip 115 forks into a first 111 and second prongs 112, resembling a pointed object, which are irregular in size, forming a substantially U-shaped or V-shaped construct thereof for manipulating a configuration and/or an orientation of the delivered lens in the eye.

Figure 3:
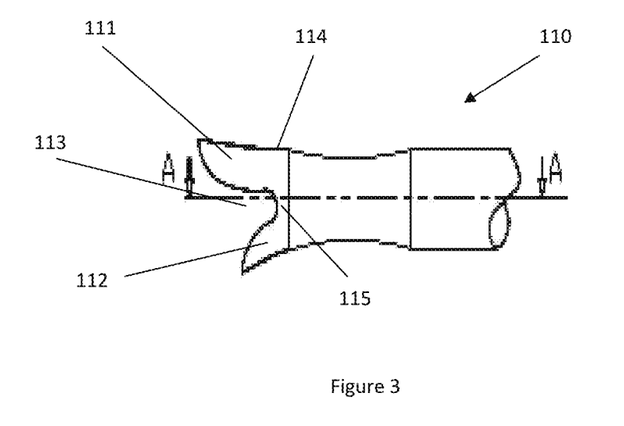
FIG. 3 shows a side view of one embodiment of a Y-shaped probe with a V- or C-shaped bifurcated tip.
Figure 4:
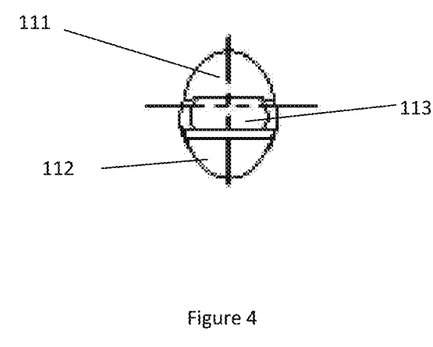
FIG. 4 shows a front cross-sectional view of the V-shaped bifurcated tip.

Preferably the probe 110, as illustrated in FIGS. 3 and 4, of the disclosed invention is fabricated from metal materials or alloy or any suitable 3D printing materials (i.e. Biocompatible PolyJet photopolymer, thermoplastics, etc) showing good mechanical strength to endure the deflective force, generated in the process of pushing the IOL out of the nozzle 150, without deformation or breakage. The material can be stainless steel, titanium, and/or another material or alloy. The probe 110 is preferably a single piece rod-like structure having a body 116, one end carrying the U-shaped or V-shaped construct and another end mounted to the plunger assembly 120 substantially aligned to the longitudinal axis of the plunger assembly 120. Length of the probe 110 is around 3 to 6 cm or any suitable length adapted to fit into the size of palm of a user (i.e. Asian, Western, etc), and the average diameter of the probe 110 ranges from 400 to 1000 µm. The probe 110 is sized to a diameter smaller than the incision made in the cornea in order to be inserted into the posterior chamber of the eye to manipulate the delivered IOL. Moreover, the first 111 and second prongs 112 of the bifurcated tip 115 are made irregular in size relative to one another. Particularly, the first prong 111 is greater in size relative to the second prong 112. The bifurcated tip 115 as presented in FIGS. 3 and 4 has the first 111 and second prongs 112 sized in a ratio of 4-5:2-3 in respect to front cross-sectional view. The opposing surfaces of the prongs define a tapering space 113 to engage with the delivered IOL for manipulation of the IOL in the later stage of the operation when needed. As shown in FIG. 3, both the first 111 and second prongs 112 are tapered with a curved outline rather than a straight cut resulting the opposing surfaces of the prongs bearing greater carved angle at their free ends compared to the ends conjoined to the probe 110. More preferably, the outer surfaces of the first 111 and second prongs 112 are not coplanar with the rest of the probe 110's body 116. Instead, the outer surfaces of the first 111 and second prongs 112 respectively expanding out from the body 116 of the probe 110 have obtuse angle 114 formed in relative to the body 116 of the probe 110. The outer surface of the expanded prong 111/112 provides additional hook-like structure to facilitate the IOL manipulation. For instance, the haptic of the IOL can be hooked onto the outer surface of the prongs 111/112 and dragged the haptic to the desired orientation in the placement of the lens.

Figure 5:
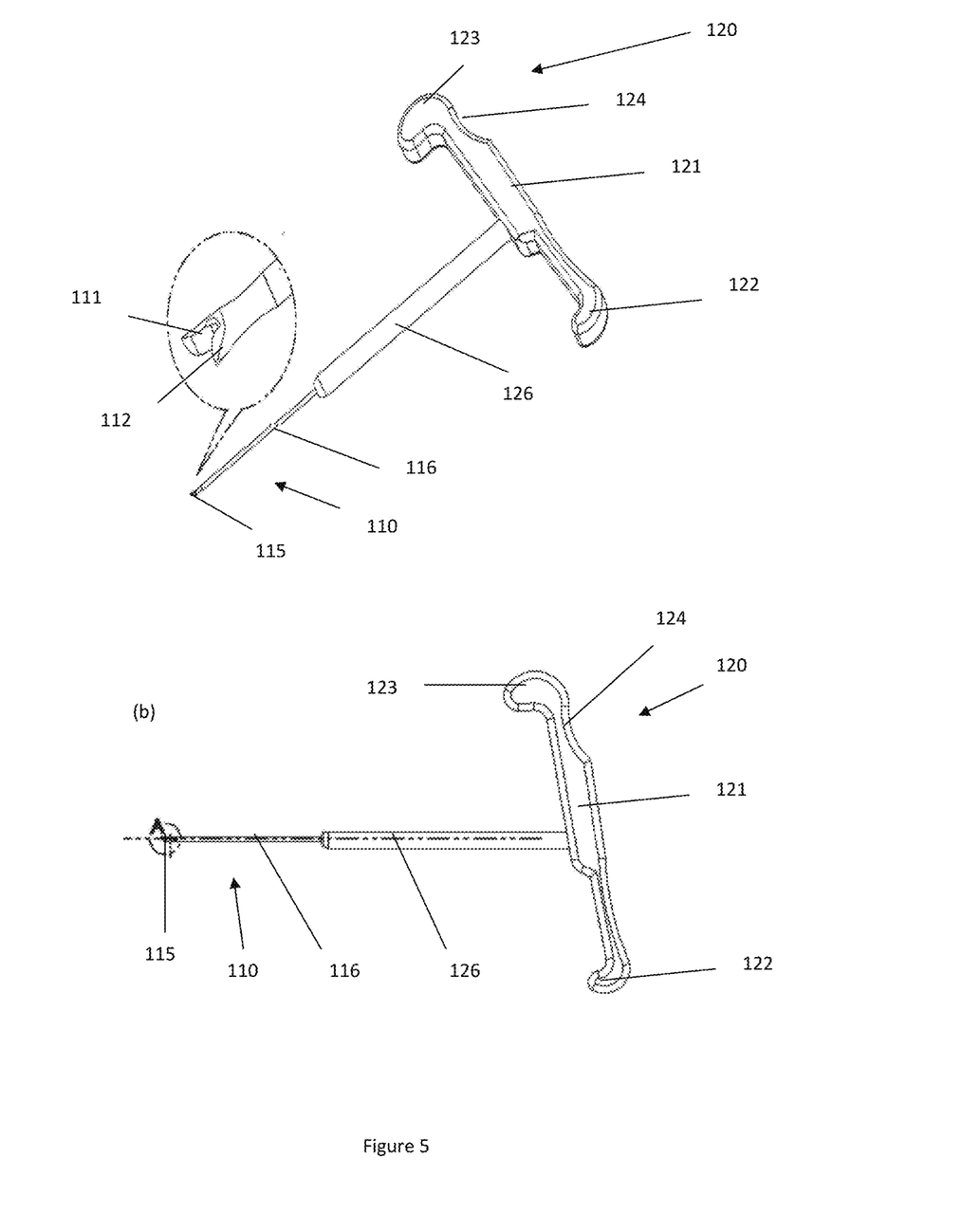
FIG. 5 illustrates (a) perspective view and (b) side cross-sectional view of a plunger assembly and a probe of the embodiment shown in FIG. 1.

Referring now to FIG. 5, one preferred embodiment of the plunger assembly 120 is shown. The plunger assembly 120 is composed of a shaft 126 having one extreme longitudinally aligned and joined to the end, which is opposing to the bifurcated tip 115, of the probe 110 and an enlarged end serving as a thumb press to regulate relative advancement of the probe 110 inside the tubular member 130. Furthermore, the plunger assembly 120 has an enlarged end disposed around the back through opening 133 to control movement of the plunger assembly 120 in relative to the tubular member 130. In contrast to the thumb press found in the conventional IOL injection tool, the enlarged end is a prolonged piece 121 possessing a front connected to the shaft 126 and a back carrying depression 124 conforming external contour of the thumb of a user that the prolonged piece 121 is fashioned to be ergonomically pressed without requiring bending of the thumb. In more specific, the plunger assembly 120 has a posterior end connected substantially median of the prolonged piece 121, exposed adjacent to the back through opening 133, expanding in perpendicular or at a tilted angle towards the plunger assembly 120 and fashioned to be pushed forth or back to control movement of the plunger assembly 120 in relative to the tubular member 130 that the plunger assembly 120 and the prolonged piece 121 collectively form a substantial T-shaped structure. More preferably, the prolonged piece 121 has the back surface of one extreme fabricated with a depression 124 to receive pushing force of the thumb of a user. As abovementioned, the prolonged piece 121 is slant towards the plunger assembly 120, more precisely the shaft 126, at a tilted angle that the extreme fabricated with the back carrying depression 124 leans against the plunger assembly 120 at a tilted angle of 60 to 85 degree. The tilted angle resembles the intuitive slight slant found in the fully extended thumb of the user. To further realize ergonomic handling of the disclosed invention, the prolonged piece 121 is fabricated to have length substantially equal to or slightly longer than the length of the thumb comply or generally comply with the contour of the thumb. Having the prolonged piece 121 scaled to the preferred length permits the thumb press to be thrust forth without demanding the user to strain or fold the thumb into an awkward posture to push the IOL through the nozzle 150. The prolonged piece 121 of one embodiment bears bulge 122/123 at its respective extreme. These bulges 122/123 enhance the mechanical integrity of the prolonged piece 121 to endure the applied pushing force from the thumb. Therefore, the bulge 123 located on the extreme which the thumb being accommodated is bigger in size compared to the one fabricated on another extreme of the prolonged piece 121. Asymmetrical in size of the bulges 122/123 and the slant of the prolonged piece 121 also visually assist the former user of the disclosed device 100 to immediately recognize the proper orientation to operate the device 100. Additionally, the bulge formed the extremes of the prolonged piece 121 stabilizes the hand of the user operating the disclosed device 100 since the bulge has increased contact surface to anchor onto the patient's facial area upon resting the operating hand and device 100 onto the face of the patient. In the most preferred embodiment, the prolonged piece 121 has both ends fabricated with increased surface area to anchor and contact onto the face of the patient.

Particularly, the user of the present invention is free from flexing the distal and proximal phalanges of the thumb in the lens delivering process. A person skilled in the art will readily understand that the word "phalanges" actually represent the finger portion inclusive of the muscle, skin, etc. The thumb press of conventional IOL injections tool mimicking syringe needs the user to flex the thumb into a relatively less ergonomic posture which generally results greater difficulty in controlling the applied force and stabilizing the hand holding the tool. More importantly, the prolonged piece 121 of the thumb press is coplanar in regards with the handle of the disclosed device 100 to further improve the ergonomic handling of the invention. Arranging the thumb press in the form of a prolonged piece 121 and coplanar in relative to the handle render the disclosed injection tool to be used and maneuvered like a gun or pistol to optimize ergonomic fitting in between the user and the disclosed invention.

According to another embodiment, the shaft 126 of the plunger assembly 120 is inserted into the hollow elongate passageway 131 defined within the tubular member 130. The telescopic movement of the shaft 126 and the tubular member 130 facilitates generation of the necessary force to inject the preloaded IOL and insertion of the bifurcated tip 115 into the incision site. The incision site is a substantially small cut at the anterior chamber of the eye. Preferably, the combined length of the probe 110 and the shaft 126 of the plunger assembly 120 is longer than the mutual length of the tubular member 130 and the secured nozzle 150 in order to have the bifurcated tip 115 protruded into the posterior chamber of the cornea to manipulate the delivered IOL. More preferably, the length of probe 110, particularly the bifurcated tip 115, can be projected out from pointed end 153 of the secured nozzle 150 is about 1 mm or less. It is possible to have the probe 110 to prod out from the secured nozzle 150 with length greater than 1 mm though it may not be necessary considering the distance in between the incision and the posterior chamber. Still, in another embodiment, the shaft 126 is fitted into the hollow elongate passageway 131 in a single orientation by having corresponding geometrical profiles fabricated lengthwise on the inner surface of the tubular member 130 defining the hollow elongate passageway 131 and the plunger assembly 120. Preferably, disclosed device 100 has the shaft 126 engraved with at least one lengthwise extending flat surface and at least one corresponding lengthwise extending flat cutout (not shown) on the inner surface of the tubular member 130 defining the hollow elongate passageway 131 that the shaft 126 has to be positioned to have the cross-section profile of the shaft 126 matching the cross-section profile of the defined hollow elongate passageway 131 in order to telescopically slide into the tubular member 130. Restraining the engagement of the tubular member 130 and the plunger assembly 120 in a single arrangement insures the disclosed device 100 can only be operable once assembled properly. For example, the tubular member 130 of one embodiment can enclose the hollow elongate passageway 131 with a D-shaped cross-section and the cross-section of the shaft 126 is D-shaped as well to enable such engagement.

Figure 6:
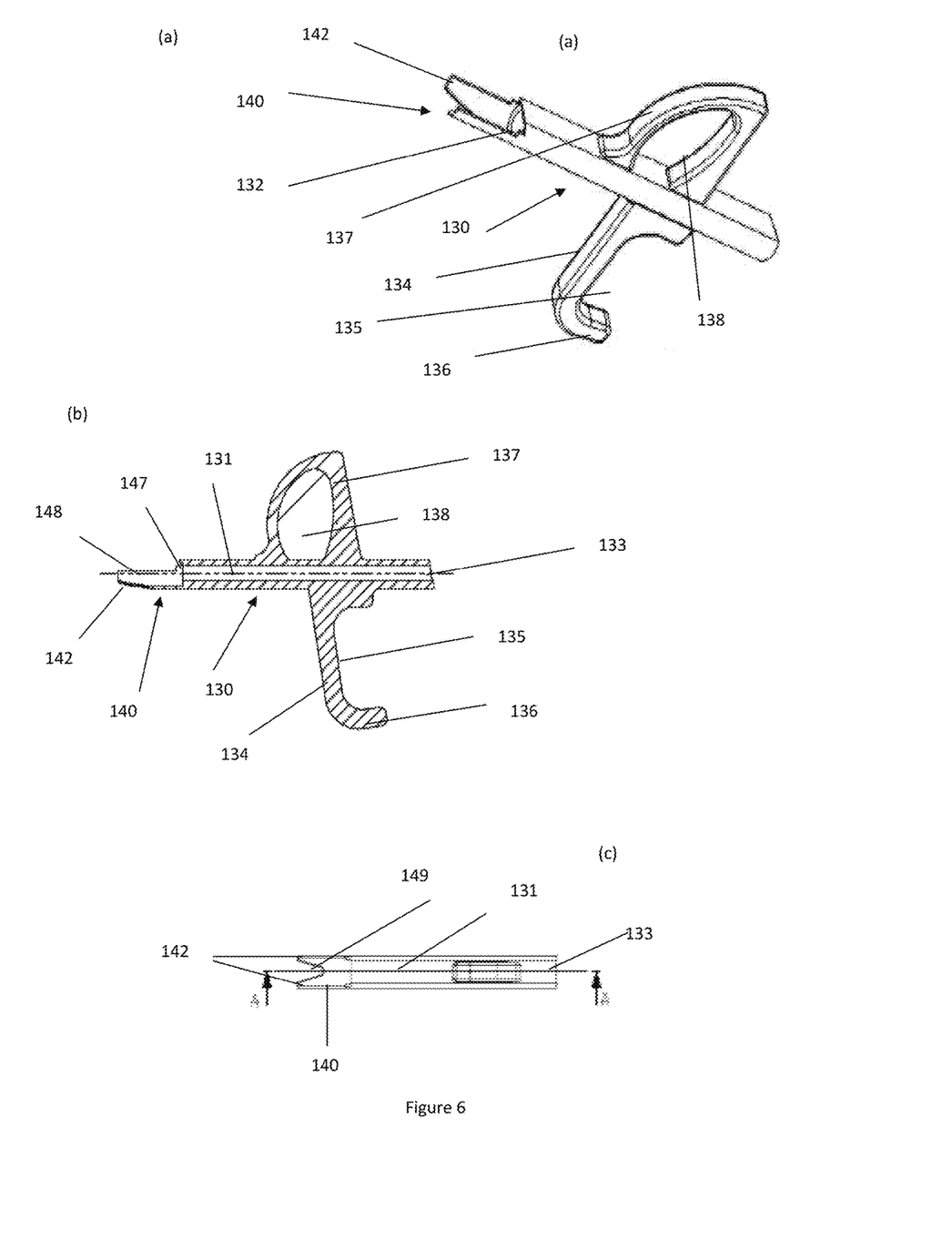
FIG. 6 illustrates (a) perspective view, (b) cross-sectional view and (c) top cross-sectional view of a tubular member incorporated with a handgrip and a handle of the embodiment shown in FIG. 1.

As in the foregoing, one preferred embodiment is adaptably maneuvered in a gun-like fashion to maximize the ergonomic fitting which inevitably leads to much steady and secured handling of the injection tool. Pursuant to the aforesaid object, the disclosed device 100 may further comprise a handgrip 134 extending from the external surface 139 of the tubular member 130 at an angle of 45 to 90 degree, more preferably 60 to 80 degree, in relative to the tubular member 130 and inclining towards the back opening 133 of the tubular member 130 as in FIGS. 6a and 6b. The inclined handgrip 134 conform intuitive flexion of the middle, ring and little finger grasped onto the handgrip 134. The handgrip 134 is preferably coplanar to the prolonged piece 121 serving as the thumb press. In addition, the backside of the handgrip 134 may have a cutout space 135 to accommodate the distal phalanges of the flexed fingers to offer better gripping onto the provided handgrip 134. Particularly, presence of the cutout space 135 allows the flexed fingers to almost fully encompass the handgrip 134 and avoid abrupt dislodgement of the held device 100. In one embodiment, the handgrip 134 carries an ergonomic profile 136 at its end, which is away from the tubular member 130, to anchor onto and substantially conform contour of the face of the patient. There are times, throughout the lens replacement procedure, that the lens injection tool is temporarily placed onto the facial area of the patient to stabilize the hand operating the device 100. The ergonomic profile 136 made available on the free end of the handgrip 134 caters better anchorage onto the facial area where the device 100 rested on. It is important to note herein as well that the handgrip 134 is fashioned to enhance the ease of lens manipulation by situating the fingers holding the disclosed device 100 at a predetermined distance. In the scenario which the fingers gripping the device 100 are located too far or too close from the protruded bifurcated tip 115, it is unlikely for the users to comfortably anchorage their hand and the held device 100 onto the patient facial area to support and stabilize the hand. Consequently, the disclosed device 100 has the handgrip 134 extending from the external surface 139 of the tubular member 130 tilted at an angle of 60 to 80 degrees towards the back through opening 133 that the handgrip 134 is configured to receive middle and ring fingers of the user to space the received fingers from the pointed end 153 of the secured nozzle 150 at a distance of 4.5 to 8 cm.

In accordance with another preferred embodiment, the disclosed device 100 further comprises a ring handle 137 formed on the external surface 139 of the tubular member 130 ascending in a direction opposite to the handgrip 134 that the ring handle 137 encloses a through hole 138 to receive index finger of a user. More specifically, the ring handle 137 is substantially in the same plane as to the handgrip 134 and the prolonged piece 121. Index finger of the user of the present invention can securely lock onto the ring handle 137 to operate the disclosed invention. Besides this, the handgrip 134 as in the aforesaid description can take the form of a ring handle as well in other embodiments.

Further, the anterior section of the tubular member 130 is incorporated with an open platform 140 to detachably fasten the secured nozzle 150. As shown in FIGS. 6b and 6c, the open platform 140 projects out from the underside edge of the tubular member 130 adjacent to the front through opening 132 with an open top where part of the secured nozzle 150 is engaged and supported. The open platform 140 preferably has the elongate sides arched upward creating a tray to hold the secured nozzle 150. Preferably, the top of the each elongate side has a front erected step 144 fabricated at the anterior section of the elongate side that an indented track 148 runs in between the edge of the front through opening 132 and the front erected step 144. Similarly, it is possible to have a pair of back erected steps 147 further formed on the elongate sides immediate to the front through opening 132 to define the indented track 148 in between the front 144 and back erected steps 147 located on the same elongate side. The portion of the open platform 140 end gradually curves upward towards it pending end forming a 5 to 15 degree raise in respect of the horizontal plane thereof. The slight raise at the pending end is made to be compatible with tapering shape of the secured nozzle 150 allowing the secured nozzle 150 to be snugly fitted onto the open platform 140 and obtains sufficient mechanical support. A substantially triangular, but not limited to, void is further carved onto the open platform 140 forming a pair of parallel running tines 142 at the pending end. The void 149 presented provides room for the open platform 140 to be gently and momentarily deformed without breaking when the secured nozzle 150 is interlocked onto the tubular member 130. Thickness of the open platform 140 is much lower than the wall of the tubular member 130 to further contribute to its deformability. Once the nozzle 150 fully engaged with the tubular member 130, the gently deformed open platform 140 shall contract to resume its original shape and tightly clamp onto the secured nozzle 150 to prevent potential disengagement.

Figure 7:
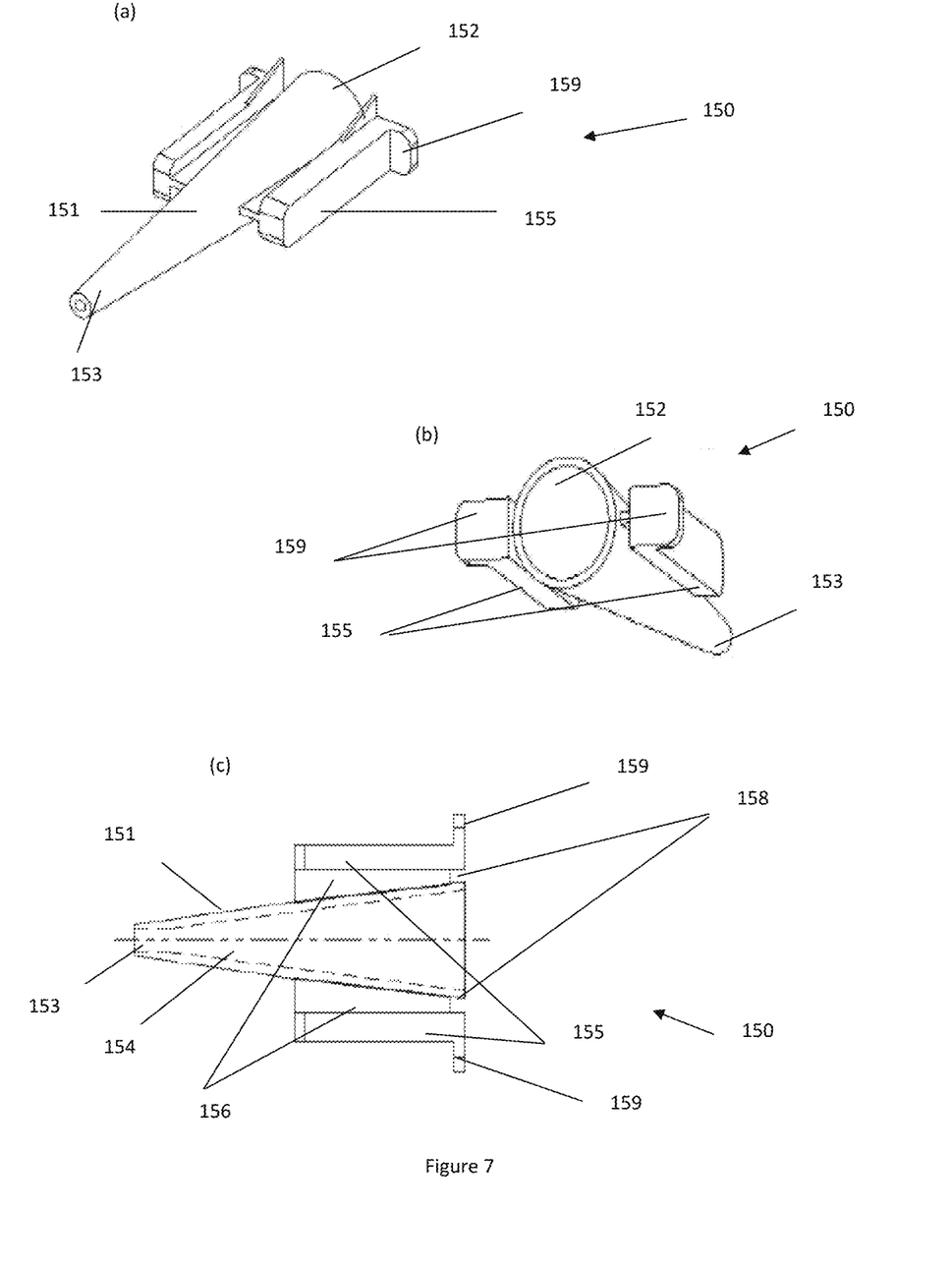
FIG. 7 illustrates the (a) front and (b) back perspective view and (c) top cross-sectional view of a nozzle or lens cartridge employed in the embodiment shown in FIG. 1.

One embodiment of the secured nozzle 150 is present in the FIGS. 7a to 7c. Specifically, the secured nozzle 150 comprises a cone structure 151 having an expanded base 152, which is mounted onto the front through opening 132 or more precisely the open platform 140 of the tubular member 130, tapering towards a pointed end 153 fashioned to be inserted into the incision. The cone structure 151 of the secured nozzle 150 encloses a lumen 154 substantially tapered from the base 152 to the pointed end 153 and the lumen 154 is aligned with the hollow elongate passageway 131 that the lens is disposed within the lumen 154 to be readily delivered. According to the preferred embodiment, the part of the lumen 154 around the pointed end 153 is made to be equivalent in size instead of being tapered. The non-tapered section of the lumen 154 ensures the pre-loaded lens is subjected to equal pressure at the final stage of the injection to avoid explosive delivery which may jeopardize the operation. A pair of lateral running ribs 155 runs in parallel at the respective opposite lateral side of the cone structure 151 that the lateral running rib 155 is attached to and spaced away from the cone structure 151 through a planar sheet 156. The length of the planar sheet 156 is approximate to the indented track 148 to be fitted in thereto. More specifically, the secured nozzle 150 is fastened onto the platform 140 by fixing the paired planar sheets 156 into the paired indented track 148. The front erected steps 144 on the platform 140 abut onto the front edges of the planar sheets 156 to prohibit forward movement and detachment of the engaged secured nozzle 150 caused by front thrusting force. Moreover, the planar sheets 156 are preferably shorter in length compared to the lateral running ribs 155 to create a recess 158 in between the expanded base 152 of the cone structure 151 and the respective lateral running rib 155 at the posterior portion of the planar sheet 156. The pair of recesses 158 is readily to receive the back erected steps 147 or edges of the front through opening 132. The size of the recesses 158 can be varied according to different embodiments of the disclosed invention. Particularly, the lateral running ribs 155 have to be spaced further away from the cone structure 151 in order to hold the edges front through opening 132. Once the back erected steps 147 or edges of the front through opening 132 are slotted into the recesses 158, the lateral running ribs 155 hinder lateral movement of the engaged secured nozzle 150 and secure the secured nozzle 150 from being dislodged. In further embodiment, the portion of the lateral running ribs 155 overlapping with the recesses 158 can be fabricated to bear extra thickness 159 to strengthen mechanical property of the lateral running ribs 155 at that particular portion. To detach the engaged secured nozzle 150, the user shall firstly push the secured nozzle 150 upward followed by pulling nozzle 150 off the tubular member 130. One skilled in the art shall appreciate the fact that it is possible to realize the engagement of the secured nozzle 150 and the tubular member 130 via various interlocking mechanisms known in the art. Any modification in the like aspect shall not depart from the scope of the present invention.

Figure 12:
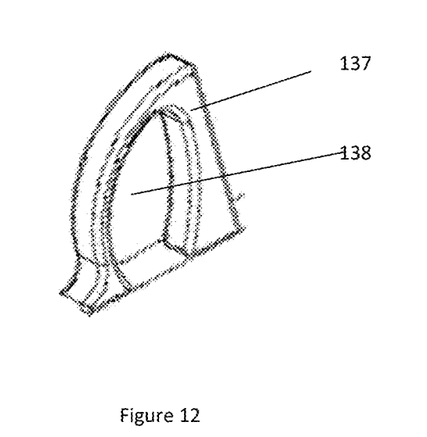
FIG. 12 shows one embodiment of a lightweight cutout handle incorporated as a portion of the disclosed device.

According to one embodiment, the disclosed device of delivering intraocular lens to an operation site of a patient comprises a tubular member defined by a hollow elongate passageway, a front and a back through opening of the passageway; a nozzle having an expanded base, which is mounted onto the front opening of the tubular member, tapering towards a pointed end fashioned to be inserted into the incision, the nozzle enclosing a lumen substantially tapered from the base to the pointed end and aligned with the passageway that the lens is disposed within the lumen to be readily delivered; an elongate probe, at least partially housed within the passageway, having a bifurcated tip which is configured to telescopically slide out from the pointed end of the nozzle pushing the disposed lens into the eye; and a driving mechanism, equipped with an actuator, mechanically engaged to the probe to move the bifurcated tip into the incision of the eye to concurrently deliver the disposed lens, wherein the bifurcated tip forks into a first and second prongs, which are irregular in size, forming a substantially U-shaped or V-shaped construct thereof for manipulating a configuration and/or an orientation of the delivered lens in the eye. The driving mechanism housed in various embodiments of the present invention for advancing the probe operates by way of a spring-based or gear-based mechanism to provide alternative control over movement of the probe into the eye. Various driving mechanisms are described in greater details henceforth. Preferably, the device itself resembles a glue gun for single handed injection of an IOL. A variety of injection mechanisms are described herein. Essentially, the injection mechanisms advance the lens forward. One of the key features is the gunlike handle outlined in FIGS. 8-9 and 12 can be placed on the patient's cheek for stability. Another key feature is a straightforward non rotating plunger which can also serve as a manipulator. The material the plunger is made from can be a disposable plastic, which is lightweight and ideally biodegradable.

Alike the foregoing embodiments, the probe is preferably a single piece rod-like structure having a body, one end carrying the U-shaped or V-shaped construct and another end mounted to the plunger assembly substantially aligned to the longitudinal axis of the plunger assembly. Most importantly, the first and second prongs of the bifurcated tips are made irregular in size to one another. Particularly, the first prong is greater in size in relative to the second prong. The bifurcated tip has the first and second prongs sized in a ratio of 4-5:2-3 in respect to front cross-sectional view. The opposing surfaces of the prongs define a tapering space to engage with the delivered IOL for manipulation of the IOL in the later stage of the operation when needed. Both the first and second prongs are tapered with a curved outline rather than a straight cut rendering the opposing surfaces of the prongs bearing greater carved angle at their free ends compared to the ends conjoined to the probe. More preferably, the outer surfaces of first and second prongs are not coplanar with the rest of the probe's body. Instead, the outer surfaces of first and second prongs respectively expanding out from the body of the probe have obtuse angle formed in relative to the body of the probe.

The disclosed inventions housing the driving mechanism are fabricated to be maneuvered in a gun-like fashion to maximize the ergonomic fitting as explained in the aforesaid description. Consequently, these embodiments share the general feature of having a handgrip extending from the external surface of the tubular member at an angle of 45 to 90 degree, more preferably 60 to 80 degree, in relative to the tubular member and inclining towards the back opening of the tubular member as illustrated. More preferably, the handgrip is located right under the back through opening. The inclined handgrip conform intuitive flexion of the middle, ring and little finger grasped onto the handgrip. The backside of the handgrip may have a cutout space to accommodate the distal phalanges of the flexed fingers to offer better gripping onto the provided handgrip. Still, the handgrip may be fabricated with an ergonomic profile at its end, which is away from the tubular member, to anchor onto and conform contour of the face of the patient. Nonetheless, a ring handle maybe formed on the external surface of the tubular member in a direction opposing to the handgrip that the ring handle encloses a through hole to receive index finger of a user according to another embodiment.

FIGS. 8 to 11 depicting the embodiments incorporated with the driving mechanism are free from showing the attached nozzle merely aiming to simplify the illustration unless mentioned otherwise. To secure attachment of the nozzle, these embodiments carry the corresponding open platform (not shown) at the immediate fore of the front through opening and the open platform has the paired indented track to lock the mounted nozzle. Preferably, one embodiment of the nozzle applicable herein generally own the like features highlighted in the abovementioned embodiments. It comprises a cone structure having an expanded base, which is mounted onto the front opening or more preferably the open platform of the tubular member, tapering towards a pointed end fashioned to be inserted into the incision. The cone structure of the nozzle encloses a lumen substantially tapered from the base to the pointed end and the lumen is aligned with the passageway that the lens is disposed within the lumen to be readily delivered. A pair of ribs runs in parallel at the respective opposite lateral side of the cone structure that the rib is attached to and spaced away from the cone member through a planar sheet. The length of the planar sheet is approximate to the indented track to be fitted in thereto. More specifically, the nozzle is fastened onto the platform by fixing the paired planar sheets into the corresponding paired indented tracks. The front erected steps on the platform abut onto the front edges of the planar sheets to prohibit forward movement and detachment of the engaged nozzle caused by front thrusting force. Moreover, the planar sheets are preferably shorter in length compared to the ribs to create a recess in between the expanded base of the cone structure and the respective lateral running rib at the posterior portion of the planar sheet. The pair of recesses is readily to receive the back erected steps or edges of the front through opening. Upon slotting the edge of the front through opening into the recesses, the ribs hinder lateral movement of the engaged nozzle and secure the nozzle from being dislodged. Typically, the open platform for detachably fastening the nozzle projects out from the underside edge of the tubular member adjacent to the front through opening with an open top where part of the nozzle is engaged and supported. The open platform preferably has the elongate sides arched upward creating a tray to hold the nozzle. The top of the each elongate side has a front erected step fabricated at the anterior section of the elongate side that an indented track runs in between the edge of the front through opening and the front erected step. In other embodiments, the open platform has a pair of erected back steps further formed on the elongate sides immediate to the front through opening create the indented track in between the front and back steps located on the same elongate side lock the mounted nozzle.

Figure 8:
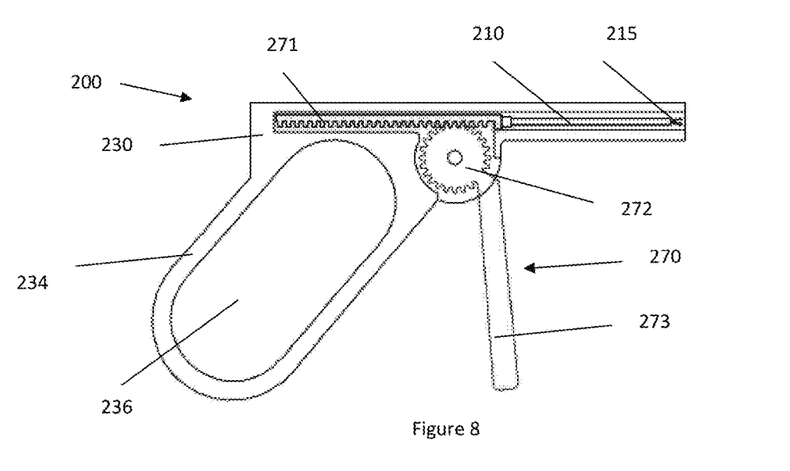
FIG. 8 shows one embodiment of the disclosed device utilizing a rack and pinion advancer with trigger movement.

Shown in the FIG. 8, the driving mechanism of the disclosed device 200 comprises a rack 271 slidably stored within the tubular member 230 to anteriorly engage with the probe 210, and a pinion 272 having one part functionally coupled to the rack 271 and the other part connected to the actuator 270 that the pinion 272 translates motion of the actuator 270 to move the rack 271 forth and back in the passageway to respectively forward and retract the probe 210 in relative to the tubular member 230. In one aspect, the actuator 270 and the pinion 272 can be an integrated piece that the actuator 270 is angled handle 273 descending from the pinion 272. Particularly, the angled handle 273 has a shorter top section projecting away from the circumference of the pinion then further descends downward to form the longer bottom section with an obtuse angle spaced in between the two sections. Cogs on the pinion 272 are interlocked with the cogs on the rack 271 that pulling the actuator 270, precisely the angled handle 273, closer to the handgrip 234 results in forward movement of the probe 210 towards the front though opening pushing along the disposed IOL, via the bifurcated tip 215, out of the nozzle into the eye. The handgrip 234 of this embodiment can be in the form of a ring handgrip encompassing a through space 236 at the middle. Or, in another embodiment, a cutoff can be included at the back of the handgrip as well.

Figure 9:
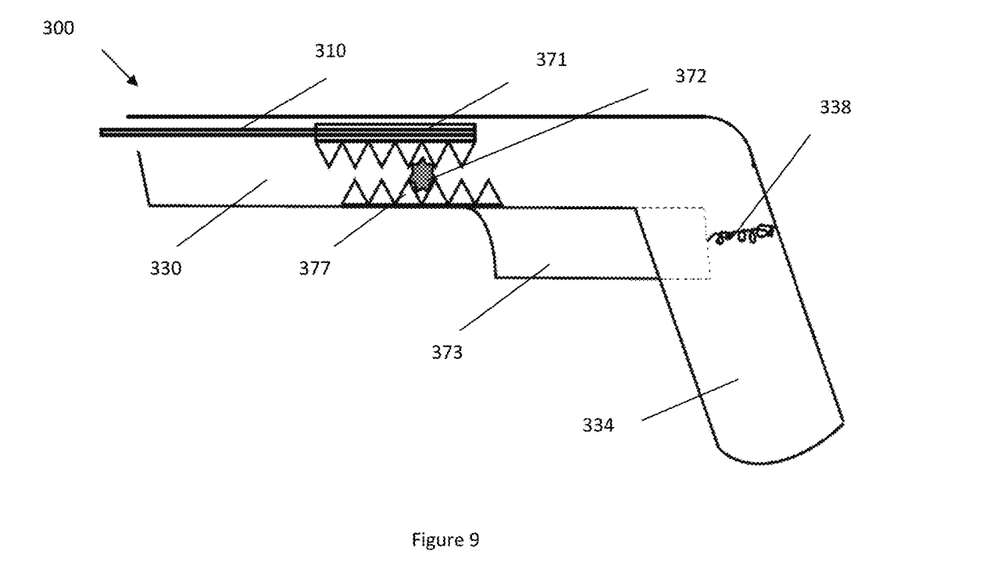
FIG. 9 shows another embodiment operating based on a gearing mechanism of a rack and pinion type trigger.

FIG. 9 represents another embodiment of the disclosed invention being configured to operate based upon the like rack and pinion concept. In fact, the pinion 372 is articulated in between elongate edges of two opposed facing racks, a top rack 371 and a bottom rack 377. The top rack 371 anteriorly joined to back end of the probe 310 that forward movement of the top rack 371 prods the front end, constructed with the bifurcated tip, of the probe 310 to the front through opening. The elongate edge of the bottom rack 377 free from the cog attached to one side of the actuator 373 while the remaining of the actuator exposed at the underside of the tubular member 330 and at the front side of the handgrip 334. The underside of the tubular member 330 has a lengthwise stretched slot (not shown) to permit the actuator 373 to be pressed against the handgrip 334. Pressing the actuator 373 towards the handgrip 334 moves the bottom rack 377 backward and, concurrently, rotates the pinion 372. Engagement of the pinion 372 and top rack 371 translates the rotation movement into a frontward movement of the top rack 371 and the joined probe 310. Employing of the two opposite racks 371/377 and a pinion 372 realizes progressive advancement of the probe 310 in delivery of the IOL and into the incised eye. In another preferred embodiment, the device 300 preferably connects the actuator 373 to a spring element 338 stored inside the device which has the spring elements 338 configured to restore the actuator 373 to its original position in the absence of external applied force. More preferably, the spring element 338 retracts the forwarded probe 310 back to its original location within the passageway as well in tandem with restoration of the actuator 373.

Figure 10:
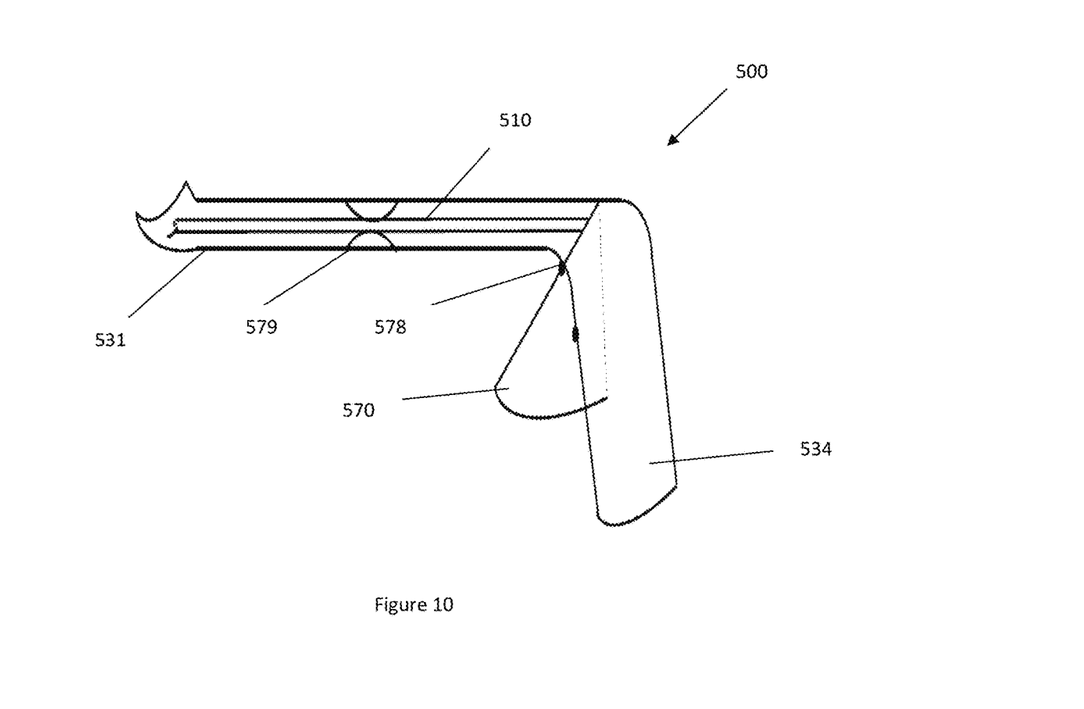
FIG. 10 shows another embodiment of the disclosed device employing a pivot point of the device to adjust and offer different levels of gearing of the advancement of a probe or plunger.

Apart from using rack and pinion, another embodiment of the disclosed capable of conducting the progressive advancement of the probe is shown in FIG. 10. The driving mechanism of this particular embodiment preferably pivotally fixes the actuator 570 onto the device at one hinged point 578 to have one end of the actuator secured with the posterior end of the probe 510 and another end of the actuator readily subjected to an external force to lever the forth and back movement of the probe 510 in relative to the tubular member. The segment of the actuator subjected to manipulation is preferably positioned in front of the handgrip 534 and to be drawn closer to the handgrip 534 to forward the probe. The passageway 531 preferably includes a holder 579 also to secure the position of the probe 510 enclosed within. The holder 579 restrains any movement of the probe 520 within the passageway 531 except the forth and back movement triggered by the actuator 570.

Figure 11:
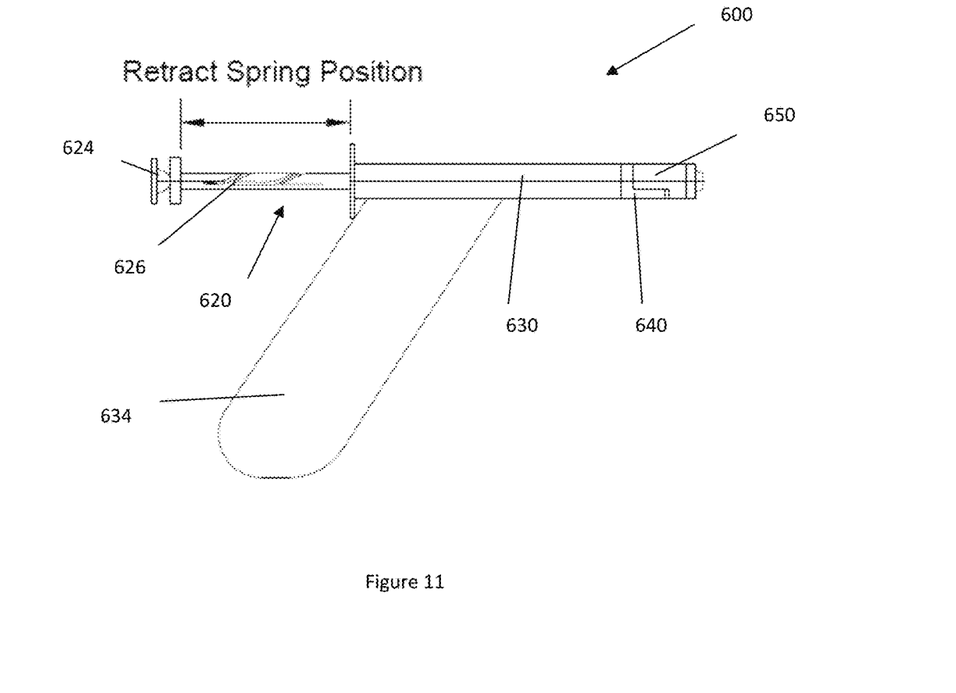
FIG. 11 shows one embodiment featuring advancement of a probe to be triggered with a thumb push type advancer.

FIG. 11 shows further embodiment 600 of the disclosed device operating in a spring-based driving mechanism. The driving mechanism preferably has a plunger 620 carrying an elongate pole 626 inserted into the passageway via the back through opening to anteriorly engage with the probe and a thumb press 624 fabricated at the posterior end of the plunger 620 that a resilient member (not shown) housed inside the tubular member 630 is fashioned to be deformably pressed into a contracted state succeeding a forward movement of the plunger 620 in the presence of a pushing force at the thumb press and resume its original state to retract the plunger upon removal of the pushing force. Particularly, the resilient member refers to, but not limited to, coil spring having the elongate pole 626 passing through its longitudinal axis and wrapping around the external surface of the pole 626. The external surface of the pole 626 is constructed with a back chock to stop the resilient member to slide off from the posterior end of the pole 626. Correspondingly, a front chock is fabricated inside the passageway to prevent the resilient member to glide out of the passageway from the front through opening. The coil spring spans in between the front and back chocks that the pushing force applied onto the thumb press 624 shall cause the front and back end of the coil spring to abut onto the front and back chocks respectively followed by contraction of the coil spring. Once the pushing force is removed, the coil spring spontaneously resumes its original configuration and retracts the plunger 620 along. The front end of the tubular member 630 is equipped with an open platform 640 to fasten the nozzle 650. The handgrip 634 extends downward from the external surface of the tubular member 630 at an obtuse angle around 90 to 140 degrees in relative to the fastened nozzle 650.

The present disclosure includes as contained in the appended claims, as well as that of the foregoing description. Although this invention has been described in its preferred form with a degree of particularity, it is understood that the present disclosure of the preferred form has been made only by way of example and that numerous changes in the details of construction and the combination and arrangements of parts may be resorted to without departing from the scope of the invention.

The invention claimed is:

1. A device for delivering intraocular lens through an incision on an eye of a patient comprising:
    a tubular member defining a hollow elongate passageway accessible by a front and a back through opening;
    a nozzle having an expanded base, which is mounted to the front through opening of the tubular member, tapering towards a pointed end, the nozzle enclosing a lumen substantially tapered from the base to the pointed end and the lumen being aligned with the passageway that the lens is disposed within the lumen to be readily delivered;
    an elongate probe, at least partially housed within the passageway, having a bifurcated tip which is configured to telescopically slide out from the pointed end of the nozzle to push the disposed lens into the eye; and
    a plunger assembly having a shaft inserted into and moveable within the passageway to anteriorly engage with the probe to move the probe in relative to the tubular member, wherein the bifurcated tip forks into a first and second prongs, which are irregular in size, forming a substantially U-shaped or V-shaped construct thereof for manipulating a configuration and/or an orientation of the delivered lens in the eye.

2. The device of claim 1, wherein the first and second prongs are sized in a ratio of 18-15:12-6.

3. The device of claim 1, wherein the plunger assembly has an enlarged end disposed around the back through opening to control movement of the plunger assembly relative to the tubular member.

4. The device of claim 1, wherein the plunger assembly has a posterior end connected substantially median of a prolonged piece, located outside of the passageway adjacent to the back through opening, expanding in perpendicular to the plunger assembly and fashioned to be pushed forth or back to control movement of the plunger assembly relative to the tubular member that the plunger assembly and the prolonged piece collectively form a T-shaped structure.

5. The device of claim 4, wherein the prolonged piece has the back surface of one extreme fabricated with a depression to receive pushing force of the thumb of a user.

6. The device of claim 4, wherein the prolonged piece has both ends fabricated with increased surface area to anchor and contact onto the face of the patient.

7. The device of claim 1, wherein the shaft is fitted into the passageway in a single orientation by having corresponding geometrical profiles fabricated lengthwise on the inner surface of the tubular member defining the passageway and the shaft.

8. The device of claim 1 further comprising a handgrip extending from the external surface of the tubular member with an angle of 60 to 80 degrees formed relative to the portion of the tubular member directing towards the front through opening.

9. The device of claim 8, wherein the handgrip carries an ergonomic profile at its end, which is away from the tubular member, to anchor onto and substantially conform contour of the face of the patient.

10. The device of claim 8 further comprising a ring handle formed on the external surface of the tubular member in a direction opposing the handgrip wherein the ring handle encloses a through hole to receive index finger of a user.

11. The device of claim 1 further comprising a handgrip extending from the external surface of the tubular member with an angle of 60 to 80 degrees formed relative to the portion of the tubular member directing towards the front through opening, wherein the handgrip is configured to receive middle and ring fingers of the user to space the received fingers from the pointed end of the nozzle at a distance of 4.5 to 8 cm.

12. The device of claim 1, wherein the first and second prongs collectively define an angle of between 60 to 100 degrees.

13. The device of claim 1, wherein a driving mechanism has a plunger carrying an elongate pole slidably inserted into the passageway via the back through opening to anteriorly engage with the probe and a thumb press fabricated at the posterior end of the plunger that a resilient member housed inside the tubular member is fashioned to be deformably pressed into a contracted state succeeding a forward movement of the plunger in the presence of a pushing force at the thumb press and resume its original state to retract the plunger upon removal of the pushing force.

* * * * *